(12) United States Patent
Hwang et al.

(10) Patent No.: US 9,988,362 B2
(45) Date of Patent: Jun. 5, 2018

(54) METHOD FOR PREPARING FURAN DERIVATIVES FROM BIOMASS

(71) Applicant: KOREA RESEARCH INSTITUTE OF CHEMICAL TECHNOLOGY, Daejeon (KR)

(72) Inventors: Dong Won Hwang, Daejeon (KR); Pravin P. Upare, Daejeon (KR); Jong San Chang, Daejeon (KR); Young Kyu Hwang, Daejeon (KR); U Hwang Lee, Daejeon (KR); Do Young Hong, Gyeonggi-do (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days. days.

(21) Appl. No.: 15/098,905

(22) Filed: Apr. 14, 2016

(65) Prior Publication Data

US 2016/0304480 A1 Oct. 20, 2016

(30) Foreign Application Priority Data

Apr. 15, 2015 (KR) .......................... 10-2015-0053134

(51) Int. Cl.
*C07D 307/42* (2006.01)
*C07D 307/36* (2006.01)
*C07D 307/48* (2006.01)
*C07D 307/50* (2006.01)

(52) U.S. Cl.
CPC ......... *C07D 307/42* (2013.01); *C07D 307/36* (2013.01); *C07D 307/48* (2013.01); *C07D 307/50* (2013.01)

(58) Field of Classification Search
None
See application file for complete search history.

(56) References Cited

U.S. PATENT DOCUMENTS 8,277,521 B2 * 10/2012 Gruier .................. C07D 307/46
44/350
2011/0263880 A1 10/2011 Rauchfuss et al.

FOREIGN PATENT DOCUMENTS

KR 10-2010-0061723 A 6/2010
KR 20130035167 4/2013
KR 2013-0091637 8/2013

OTHER PUBLICATIONS

Balakrishnan, et al. "Etherification and reductive etherification of 5-(hydroxymethyl)furfural: 5-(alkoxymethyl)furfurals and 2,5-bis(alkoxymethyl )furans as potential bio-diesel candidates" *Green Chem.*, 2012, vol. 14, pp. 1626-1634.
Chidambaram and Bell, "A Two-Step Approach for the Catalytic Conversion of Glucose to 2,5-dimethylfuran in Ionic Liquids," *Green Chem.*, 2010; 12: 1253-1262.
Zhong, Shaohua, et al. "Combustion and Emissions of 2,5-Dimethylfuran in a Direct-Injection Spark-Ignition Engine" Energy Fuels 2010, 24, 2891-2899.
Williams, C. Luke, et al. "Cycloaddition of Biomass-Derived Furans for Catalytic Production of Renewable p-Xylene" ACS Catalysis 2012, 2, 935-939.
Leshkov, Yuriy, et al. "Production of dimethylfuran for liquid fuels from biomass-derived carbohydrates" Nature 2007, 447, 982-986.
Kazi, Feroz, et al, "Techno-economic analysis of dimethylfuran (DMF) and hydroxymethylfurfural (HMF) production from pure fructose in catalytic processes" Chemical Engineering Journal 2011, 169, 329-338.
Zakrzewska, Malgorzata, et al. "Ionic Liquid-Mediated Formation of 5-HydroxymethylfurfuralsA Promising Biomass-Derived Building Block" Chem. Rev., 2011, 11, 397-417.
Shimizu, Ken-ichi, et al. "Enhanced production of hydroxymethylfurfural from fructose with solid acid catalysts by simple water removal methods" Catalysis Communications 2009, 10, 1849-1853.
*Journal of Catalysis*, Lercher, J.A. ed., vol. 314, May 2014, 1-170.
*ChemSusChem*, Kemeling, Guido ed., vol. 7, No. 4, Apr. 2014, 946-955.

* cited by examiner

*Primary Examiner* — Heidi Reese
(74) *Attorney, Agent, or Firm* — Norton Rose Fulbright US LLP

(57) ABSTRACT

The present invention relates to a method for preparing for a furan derivative from biomass, comprising step (1) of preparing 5-hydroxymethylfurfural by reacting biomass and a solid acid catalyst in butanol; and step (2) of preparing a furan derivative by reacting the butanol solution of 5-hydroxymethylfurfural, obtained in step (1), with a hydrogenation catalyst.

11 Claims, 2 Drawing Sheets

US 9,988,362 B2

METHOD FOR PREPARING FURAN DERIVATIVES FROM BIOMASS

CROSS-REFERENCE TO RELATED APPLICATIONS

This application claims the benefit of Korean Application No. 10-2015-0053134, filed Apr. 15, 2015. The contents of the referenced application are incorporated herein by reference.

BACKGROUND OF THE INVENTION

1. Field of the Invention

The present invention relates to a method for preparing a furan derivative from biomass, including step (1) of preparing 5-hydroxymethylfurfural by reacting biomass and a solid acid catalyst in butanol; and step (2) of preparing a furan derivative by reacting the butanol solution of 5-hydroxymethylfurfural, obtained in step (1), with a hydrogenation catalyst.

2. Description of the Related Art

With the pressing issues on the development of alternative energy sources due to high oil prices, energy security, and strengthened regulations on greenhouse gas emissions, biofuel as the next-generation fuel has been rapidly distributed. Biofuel is a sustainable energy source produced from biomass present in nature. Biomass is a fossil fuel, i.e., a useful alternative energy source that can overcome the depletion of fossil fuel i.e. carbon resources, and is a concept including all organic matters of organisms including as animals, plants, microorganisms, etc. The biomass materials include a variety of byproducts and wastes produced in agriculture and forestry including various kinds of animals and plants, food wastes, industrial wastes based on living organisms, and cultivated crops for the purpose of producing biofuels (energy crops). Additionally, biomass is a collective term referring to renewable carbon resources including starch-, cellulose-, saccharide-, and protein-wastes, organic city wastes, etc. These biomasses can be converted into biofuels in gas, liquid, and solid states by applying physical, chemical and biological techniques, and the biomass fuels have an advantage in that they are not depleted, unlike fossil fuels. Accordingly, the production of useful chemical industrial materials from biomass can provide a platform for a new sustainable green chemical industry, and in particular, the biochemical technology of converting saccharides, which can be supplied from plant resources, into various chemical materials are expected to be realized in the near future.

Dimethylfuran (hereinafter, DMF) has the properties of higher energy density and chemical stability compared to those of ethanol, and is not water-soluble and thus does not absorb moisture in the atmosphere, thus being expected as the next-generation biofuel (*Energy Fuels*, 2010, 24: 2891). Additionally, DMF is a promising compound derived from biomass that is expected to be used as a monomer for a PET polymer by a reaction with ethylene (*ACS Catal.*, 2012, 2: 935).

DMF is an intermediate and can be produced from fructose through 5-hydroxymethylfurfural (hereinafter, HMF). Specifically, DMF can be prepared by hydrogenation of particular saccharides, i.e., HMF, produced by dehydration of fructose in the presence of various acid catalysts. In particular, fructose can be obtained from glucose, which is a cellulose-forming unit structure.

Dihydroxymethyl furan (hereinafter, DHMF, or 2,5-bis (hydroxymethyl)furan; 2,5-BHF) are materials being highlighted as a monomer for a biomass-derived polymer. DHMF can be also synthesized via hydrogenation using HMF, a dehydrate of fructose, as an intermediate.

However, HMF, which is produced as an intermediate during the process of preparing the furan derivatives, has low thermal and chemical stability in an aqueous solution and thus can be easily converted into low value-added compounds such as levulinic acid and humin, after being produced in a predetermined reaction condition. Additionally, HMF has a disadvantage in that it tends to be easily transformed during a distillation process due to its very high boiling point at ambient pressure. Accordingly, the separation of HMF, which is produced by dehydration reaction of fructose and has high reactivity, from a reaction system and its subsequent use as a reactant in the DMF production process is not efficient or economical.

Accordingly, for improving the process efficiency of preparing DMF or DHMF from fructose, a method of using a biphasic reaction system by performing a dehydration reaction of fructose with a HCl catalyst in an aqueous solution, and inhibiting a secondary reaction by rapidly transporting the produced HMF using an organic extractant thereby improving the production yield of HMF from fructose was recently suggested. In particular, the HMF extracted with an organic solvent is converted into DMF by a subsequent hydrogenation reaction performed using a noble catalyst such as a CuRu/C catalyst (*Nature*, 2007, 447: 982). However, the biphasic reaction system may also accompany problems, such as an increase in energy cost due to high reaction temperature (>180° C.), a decrease in yield due to the increase of side reactions (<60%), complexity of devices and operation processes for their embodiments, difficulty in the use of a solid acid catalyst according to the use of an excess amount of NaCl additive, corrosion of a reactor due to the use of a homogenous HCl catalyst and difficulty of recovering the catalyst, inactivation of a catalyst in a HMF hydrogenation reaction by the remaining Cl ions, etc. Additionally, the DMF conversion yield of the CuRu/C catalyst used in the HMF hydrogenation reaction is about 80%, and thus there is a requirement for the development of a catalyst to improve the yield of the hydrogenation reaction, etc.

In the process of producing furan derivatives, in which HMF is prepared by the dehydration reaction of fructose and subsequently the hydrogenation reaction is performed described above, the HMF yield accounts for the highest percentage, that is, the increase of the HMF yield by 20% results in cost reduction by about 16%, and the price and the lifetime of the CuRu/C catalyst, which is used for the subsequent hydrogenation reaction, also account for relatively high percentages (*Chem. Eng. J.*, 2011, 169: 329).

Meanwhile, a technology of preparing HMF from cellulose using a homogenous catalyst such as a $CuCl_2/CrCl_2$ catalyst and an ionic liquid as a solvent has been studied (*Chem. Rev.*, 2011, 111: 397). In this process, cellulose may be used as a feed for HMF preparation, however, it has disadvantages in that an ionic liquid, which is expensive, is required as a solvent and also that the recovery of a catalyst from the product is cumbersome and difficult due to use of catalyst in the same phase. Additionally, there is also an inconvenience in that an organic solvent extractant should be additionally used for the separation of the product, HMF.

Additionally, a method of preparing HMF with a high yield of more than 95% from fructose in DMSO using a heterogeneous catalyst was reported (*Catal. Comm.*, 2009, 10: 1849). However, DMSO itself is harmful to human body and it is decomposed in a reaction condition thereby producing sulfur-containing byproducts, and thus it is impossible to employ the method in large-scale production.

SUMMARY OF THE INVENTION

The present inventors have endeavored to find a method for preparing a furan derivative from biomass, which includes fructose or glucose, with high yield and in a cost-effective manner using a solid acid as a heterogeneous catalyst. As a result, the inventors have discovered that when a dehydration reaction is performed using butanol having a melting point higher than 100° C. as a solvent along with a solid acid catalyst, the reaction can be performed at high temperature up to about 110° C., and thus HMF, which is an intermediate, can be prepared with high yield and high selectivity, thus capable of removing the solid acid and the unreacted feed by filtration alone, and that the solvent can be easily separated by fractional distillation due to a large difference in boiling point between the solvent and the furan derivative, which is the final product, and the reaction mixture solution can be used as a feed in the subsequent hydrogenation reaction not necessitating the removal of the solvent from the intermediate and the process can be simplified, thereby completing the present invention.

In order to achieve the objects of the present invention, in a first aspect, the present invention provides a method for preparing a furan derivative from biomass, including step (1) of preparing HMF by reacting biomass and a solid acid catalyst in butanol, and step (2) of preparing a furan derivative by reacting the butanol solution of HMF, obtained in step (1), with a hydrogenation catalyst.

In a second aspect, the present invention provides a method for preparing HMF, including reacting biomass and a solid acid catalyst in butanol.

In a third aspect, the present invention provides a method for preparing a furan derivative, including reacting HMF dissolved in butanol with a hydrogenation catalyst.

The present invention has been made to solve the disadvantage that, due to low thermal and chemical stability of HMF (an intermediate), the use of a water-containing solvent can easily convert HMF into a byproduct such as levulinic acid or humin by a side reaction under a dehydration reaction condition in the presence of an acid catalyst, and the disadvantage that the use of an inorganic solvent such as THF instead of water to prevent the above disadvantage cannot sufficiently increase the reaction temperature due to a low boiling point (about 66° C.) and high volatility of the solvent, thus resulting in a low reaction rate and subsequently producing a low yield. In particular, the present inventors have confirmed that when butanol, which has a boiling point of higher than 100° C., is used as a solvent, the reaction temperature can be increased to 50° C. or higher up to 110° C., even at ambient pressure, and thus the reaction rate can be significantly increased thereby enabling efficient production. Additionally, the present inventors have also confirmed for the first time that the biomass as a reactant, e.g., fructose, has low solubility to these solvents at room temperature and thus the solid acid and unreacted feed can be removed simultaneously by simple filtration after lowering the temperature upon completion of the reaction. Additionally, butanol has a boiling point higher than that of the furan derivative, which is the final product (e.g., dimethylfuran) by about 16° C. to 26° C., while having a boiling point lower than that of dihydroxymethylfuran by more than 100° C., and thus butanol can be separated by simple distillation. Accordingly, the reaction mixture solution, in which the unreacted feed and the solid acid catalyst were removed, can be used as a feed for hydrogenation reaction, which is followed without additional treatment, thus capable of considerably simplifying the series of processes for producing furan derivatives from biomass via HMF. As a result, the present inventors provide a method for preparing furan derivatives with high yield by an easy and economical process.

The furan derivative that can be prepared by the method of the present invention may be dimethylfuran or dihydroxymethylfuran. In particular, for the hydrogenation catalyst, a heterogeneous catalyst containing at least one metal component selected from the group consisting of Ru, Pt, Au, Pd, Cu, and Ni may be used. Preferably, Ru—Sn/ZnO and Au/Al$_2$O$_3$ may be used for dimethylfuran and dihydroxymethylfuran, respectively, but is not limited thereto.

For example, the biomass may include fructose, glucose, or both.

For example, when glucose is included as the biomass, an isomerization catalyst for converting glucose into fructose may be further included.

For example, the solid acid catalyst may be bronsted acid, Lewis acid or a mixture thereof. Preferably, the solid acid catalyst may be selected according to the type of biomass used in the reaction. For example, when the solid acid catalyst reacts with glucose, a mixture of Lewis acid and bronsted acid may be used, whereas when the solid acid catalyst reacts with fructose, bronsted acid may be used, but is not limited thereto.

For example, the solid acid catalyst may be an ion exchange resin type, but is not limited thereto.

For example, the butanol may be 1-butanol or isobutanol having a boiling point of 118° C. and 108° C., respectively. As such, since 1-butanol and isobutanol have boiling points higher than 100° C., they can increase the reaction temperature in step (1) to 50° C. or higher at ambient pressure, preferably to a temperature from 100° C. to 110° C., and thus they can significantly increase the rate of dehydration reaction by a solid acid catalyst. The 1-butanol and isobutanol can exhibit high chemical stability in the subsequent hydrogenation reaction of step (2) as well as in the process of HMF preparation. In the case of other butanols such as 2-butanol and tert-butanol, although they have the same molecular weight, they have disadvantages in that they have low boiling point of 100° C. or below and high water solubility.

For example, step (1) may be performed at a temperature from 50° C. to 110° C. under ambient pressure. The reaction rate may be improved by increasing the reaction temperature but when the reaction temperature exceeds 110° C., HMF selectivity may be reduced.

For example, when HMF is prepared by dehydration reaction of fructose or glucose at 100° C. or above using butanol as a solvent, the water produced therefrom can form an azeotrope with butanol, and thus the conversion of water-vulnerable HMF into a byproduct such as levulinic acid or humin by reaction with the water can be minimized by continuously separating the produced water along with butanol from the reaction system, thereby improving the yield.

For example, the biomass and the butanol may be used at a weight ratio of from 1:1 to 1:100. When the concentration of the biomass exceeds 50 wt %, the selectivity on the reaction products in step (1) reaction may be reduced.

Step (1-1), which relates to removal of the solid acid catalyst and the unreacted biomass from the reaction mixture of step (1), may be further included before step (2).

The biomass, which was used as a reactant (e.g., fructose or glucose), has low solubility in butanol at room temperature, and thus the remaining unreacted fructose or glucose may be precipitated when the temperature of the reaction solution is decreased to room temperature upon completion of the reaction. The solid acid, unreacted fructose and/or glucose may be simultaneously separated from the reaction mixture solution via filtration after cooling the reaction solution to room temperature. Preferably, step (1-1) may be achieved via filtration at a temperature from 10° C. to 50° C., but is not limited thereto. In particular, the separated solid acid and the unreacted biomass can be recycled for the HMF preparation.

Step 2 relates to the conversion of HMF (an intermediate) into a furan derivative (a final product) by reacting with a hydrogenation catalyst, and the reaction may be performed by injecting the solution, from which the solid acid catalyst and the unreacted biomass were removed through step (1-1), into a reactor filled with the hydrogenation catalyst. For the hydrogenation catalyst, any hydrogenation catalyst kwon in the art may be used without limitation, and in particular, the conditions for hydrogenation reaction may be controlled according to the type of the selected catalyst. For the hydrogenation catalyst, a catalyst containing ruthenium (Ru) or $Au/Al_2O_3$ as an active ingredient may be used, although not limited thereto.

For example, step (2-1), which relates to the separation of a furan derivative from butanol, may be further included after step (2). The butanol used as a solvent evaporates at a temperature exceeding 100° C. For example, the boiling points of 1-butanol and isobutanol, as examples of butanol, are 118° C. and 108° C., respectively, whereas the boiling point of the furan derivative (the product), e.g., dimethylfuran, is in the range of from 92° C. to 94° C., which is lower by 26° C. and 16° C., respectively, and the boiling point of dihydroxymethylfuran is about 275° C., which is significantly higher than the boiling points of the solvents. Accordingly, step (2-1), which relates to separation of the furan derivative from the solvent, may be performed via fractional distillation using the difference in boiling point and crystallization, but is not limited thereto.

Advantageous Effects of the Invention

The furan derivatives according to the present invention, e.g., DMF and DHMF, may be prepared from the biomass containing fructose or glucose using a solid acid, which is a heterogeneous catalyst, and uses butanol, and specifically the butanol having a boiling point of 100° C. or higher as a solvent, and thus it is possible to 1) perform a reaction at high temperature, 2) easily remove the solid acid and the unreacted feed, and 3) use the reaction mixture solution as the feed for the hydrogenation reaction followed subsequently, without requiring the removal of the solvent from the intermediate produced, because the solvent can be easily separated due to the large difference in boiling point between DMF and DHMF, thereby simplifying the process, thus being applicable to large-scale production of DMF and DHM.

DETAILED DESCRIPTION OF THE PREFERRED EMBODIMENTS

Hereinafter, the present invention will be described in more detail with reference to the following Examples. However, these Examples are for illustrative purposes only, and the invention is not intended to be limited by these Examples.

Example 1: Preparation of HMF from Fructose

Figure 1:
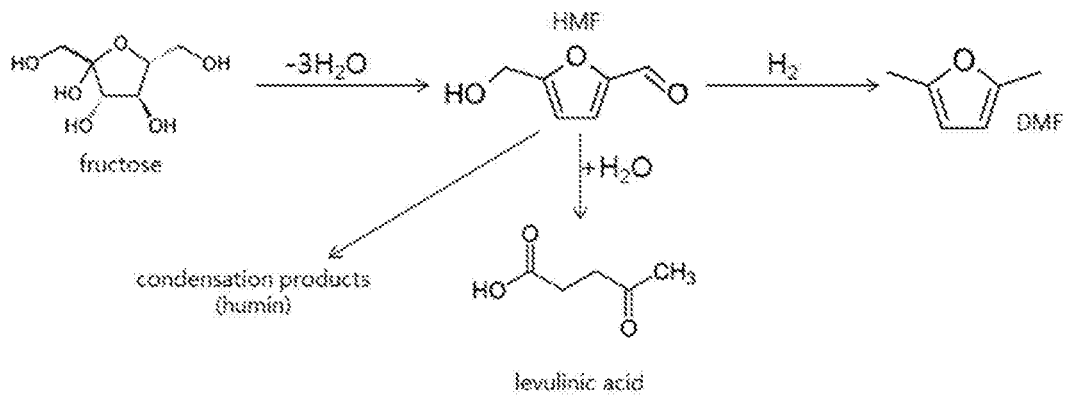
FIG. 1 shows a reaction pathway for preparing dimethylfuran from fructose.
Figure 2:
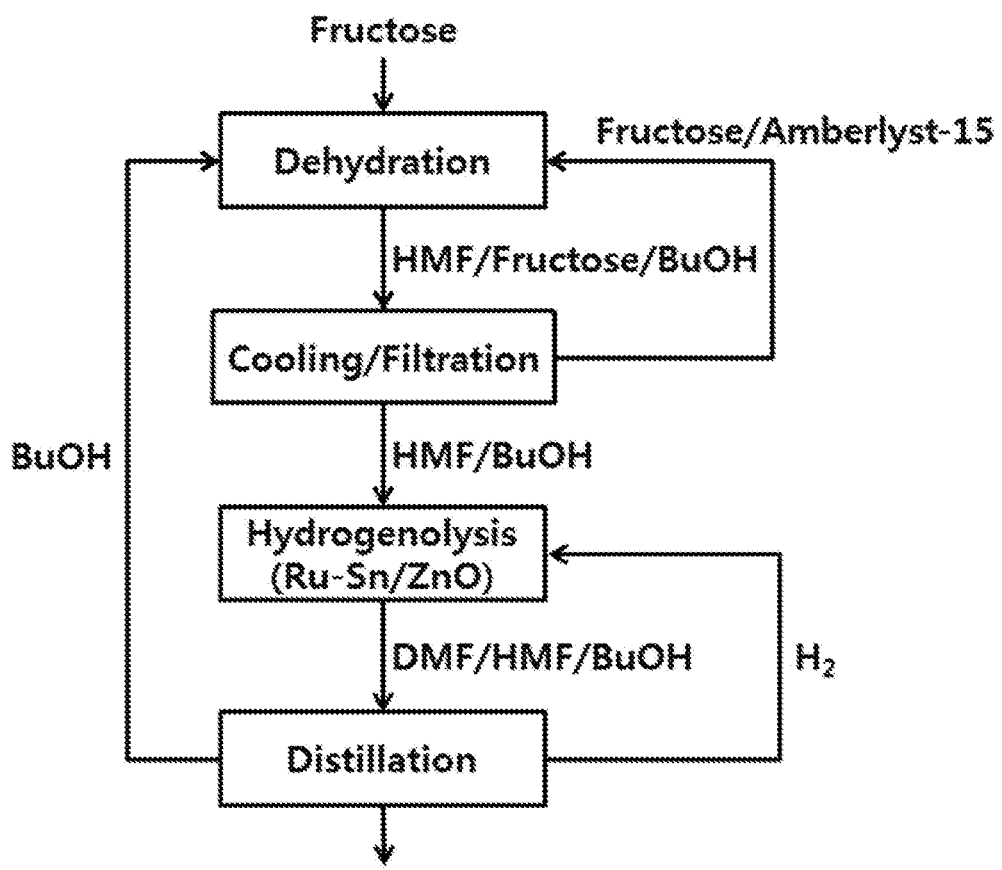
FIG. 2 shows a schematic diagram illustrating the process of preparing dimethylfuran from fructose according to the present invention.
Figure 3:
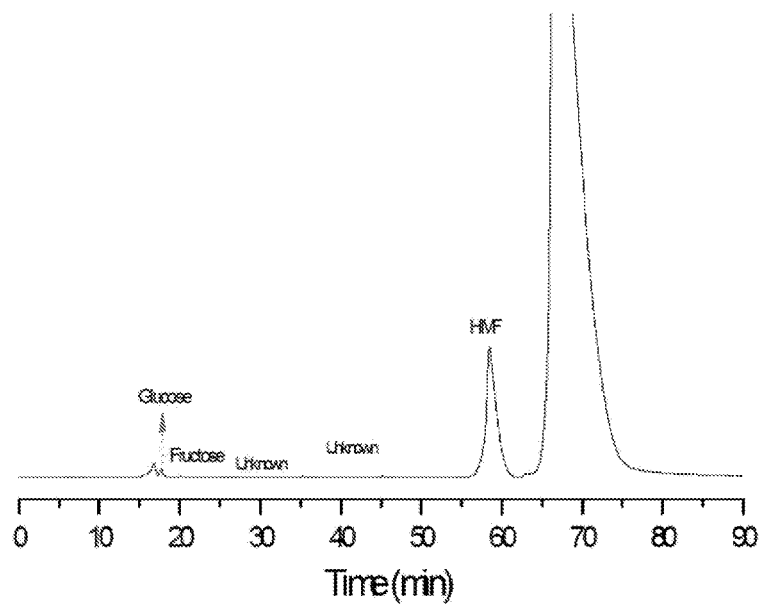
FIG. 3 shows a graph confirming the result of the preparation of HMF from fructose according to Example 1 of the present invention via liquid chromatography.

Fructose (15 g) was mixed with 1-butanol (100 g) and Amberlyst-15 resin (1 g) and reacted by heating at 100° C. for 5 hours to prepare HMF. Upon reaction, the resulting solution was cooled to room temperature and then filtered to separate Amberlyst-15 resin from the reaction mixture solution. The separated reaction mixture solution was analyzed via liquid chromatography and the results are shown in FIG. 1. In particular, the yield of the synthesized HMF was 90%.

Example 2: HMF Preparation from Fructose According to Reaction Temperature (1)

Fructose (15 g) was mixed with 1-butanol (100 g) and Amberlyst-15 resin (1 g) and reacted by heating at 110° C. for 5 hours to prepare HMF. Upon reaction, the resulting solution was cooled to room temperature and then filtered to separate Amberlyst-15 resin from the reaction mixture solution. The separated reaction mixture solution was analyzed via liquid chromatography and the resulting yield of the synthesized HMF was 87%.

Example 3: HMF Preparation from Fructose According to Reaction Temperature (2)

Fructose (15 g) was mixed with 1-butanol (100 g) and Amberlyst-15 resin (1 g) and reacted by heating at 90° C. for 5 hours to prepare HMF. Upon reaction, the resulting solution was cooled to room temperature and then filtered to separate Amberlyst-15 resin from the reaction mixture solution. The separated reaction mixture solution was analyzed via liquid chromatography and the yield of the synthesized HMF was 71%.

Example 4: HMF Preparation from Fructose According to Reaction Time

Fructose (10 g) was mixed with 1-butanol (100 g) and Amberlyst-15 resin (1 g) and reacted by heating at 100° C. for 4 hours to prepare HMF. Upon reaction, the resulting solution was cooled to room temperature and then filtered to separate Amberlyst-15 resin from the reaction mixture solution. The separated reaction mixture solution was analyzed via liquid chromatography and the resulting yield of the synthesized HMF was 91%.

Example 5: HMF Preparation from Fructose According to Resin Type

Fructose (15 g) was mixed with 1-butanol (100 g) and Amberlyst-36 resin (1 g) and reacted by heating at 100° C. for 5 hours to prepare HMF. Upon reaction, the resulting solution was cooled to room temperature and then filtered to separate Amberlyst-36 resin from the reaction mixture solution. The separated reaction mixture solution was analyzed via liquid chromatography and the resulting yield of the synthesized HMF was 83%.

Example 6: HMF Preparation from Fructose Using Isobutanol

Fructose (15 g) was mixed with isobutanol (100 g) and Amberlyst-15 resin (1 g) and reacted by heating at 100° C. for 5 hours to prepare HMF. Upon reaction, the resulting solution was cooled to room temperature and then filtered to separate Amberlyst-15 resin from the reaction mixture solution. The separated reaction mixture solution was analyzed via liquid chromatography and the resulting yield of the synthesized HMF was 88%.

Example 7: Recycling of a Solid Acid Catalyst in HMF Preparation from Fructose The Amberlyst-15 resin used in the preparation of HMF in Example 1 was recovered after separation from the reaction mixture solution, mixed with fructose (15 g) and 1-butanol (100 g), and reacted by heating at 100° C. for 5 hours to prepare HMF. Upon reaction, the resulting solution was cooled to room temperature and then filtered to separate Amberlyst-15 resin from the reaction mixture solution. The separated reaction mixture solution was analyzed via liquid chromatography and the resulting yield of the synthesized HMF was 90%.

Example 8: HMF Preparation from Glucose

Glucose (15 g) was mixed with 1-butanol (100 g), Sn-beta zeolite (1 g), and Amberlyst-15 resin (1 g) and reacted by heating at 130° C. for 5 hours to prepare HMF. Upon reaction, the resulting solution was cooled to room temperature and then filtered to separate Sn-beta zeolite and Amberlyst-15 resin from the reaction mixture solution. The separated reaction mixture solution was analyzed via liquid chromatography and the resulting yield of the synthesized HMF was 60%.

When glucose was used instead of fructose, HMF could be prepared in high yield from glucose in the presence of 1-butanol solvent was possible using an isomerization catalyst, such as Sn-beta zeolite, along with a dehydration catalyst.

Example 9: DMF Preparation from HMF (1)

A reaction was performed for 300 hours by filling a fixed bed reactor with a Ru—Sn/ZnO hydrogenation catalyst and maintaining the reactor at 240° C. under ambient pressure while supplying a reaction mixture solution containing the HMF obtained in Example 1 under the condition of WHSV 0.2/h. Upon completion of the reaction, the resulting solution was analyzed via gas chromatography and the resulting yield of the synthesized DMF was 98%.

Example 10: DMF Preparation from HMF (2)

A reaction was performed for 2 hours by filling a high-pressure batch reactor with 100 mL of the reaction mixture solution containing HMF obtained in Example 1 and a Ru—Sn/ZnO hydrogenation catalyst (1.0 g) while maintaining the temperature and the pressure at 180° C. and 10 bar, respectively. Upon completion of the reaction, the resulting solution was analyzed via gas chromatography and the resulting yield of the synthesized DMF was 95%.

Example 11: DHMF Preparation from HMF

A reaction was performed for 2 hours by filling a high-pressure batch reactor with 100 mL of the reaction mixture solution containing HMF obtained in Example 1 and an Au (1 wt %)/$Al_2O_3$ catalyst (1.0 g) while maintaining the temperature and the pressure at 140° C. and 40 bar, respectively. Upon completion of the reaction, the resulting solution was analyzed via gas chromatography and the resulting yield of the synthesized DHMF was 90%.

From Examples 9 to 11, it was confirmed that the HMF, which was prepared from fructose using the solid acid catalyst of an ion exchange resin type in the presence of 1-butanol solvent, can be directly used as a reactant for the subsequently following hydrogenation reaction, without additional treatment except for removing the catalyst by filtration, thereby capable of preparing DMF and DHMF in high yield.

Comparative Example 1: HMF Preparation from Fructose Using a Homogeneous Catalyst Fructose (15 g) was mixed with 1-butanol (100 g) and $H_2SO_4$ (0.25 g), and reacted by heating at 100° C. for 5 hours to prepare HMF. Upon reaction, the resulting solution was cooled to room temperature and analyzed via liquid chromatography. As a result, it was confirmed that the fructose conversion was 95% and the yield of the synthesized HMF was 70%.

Conclusively, even when 1-butanol was used as a solvent, the use of a homogeneous catalyst, such as $H_2SO_4$, significantly reduced the HMF yield and also caused a difficulty in separating the catalyst from the reaction mixture solution after the reaction.

Comparative Example 2: HMF Preparation from Fructose Using DMSO Solvent

Fructose (15 g) was mixed with DMSO (100 g) and Amberlyst-15 resin (1 g), and reacted by heating at 100° C. for 5 hours to prepare HMF. Upon reaction, the resulting solution was cooled to room temperature and then filtered to separate Amberlyst-15 resin from the reaction mixture solution. The separated reaction mixture solution was analyzed via liquid chromatography and the resulting yield of the synthesized HMF was 72%.

Conclusively, the HMF yield was much lower when using DMSO as a solvent compared to when using 1-butanol as a solvent, although the same solid acid catalyst was used. Additionally, since fructose is dissolved in DMSO, there was a difficulty in separating the unreacted fructose from the reaction mixture solution after the reaction.

Comparative Example 3: HMF Preparation from Fructose Using a Water Solvent

Fructose (15 g) was mixed with water (100 g) and Amberlyst-15 resin (1 g), and reacted by heating at 100° C. for 5 hours to prepare HMF. Upon reaction, the resulting solution was cooled to room temperature and then filtered to separate Amberlyst-15 resin from the reaction mixture solution. The separated reaction mixture solution was analyzed via liquid chromatography and the resulting yield of the synthesized HMF was 41%.

Conclusively, the HMF yield was much lower when using water as a solvent compared to when using 1-butanol as a solvent, although the same solid acid catalyst was used. Additionally, since fructose is dissolved in water, there was a difficulty in separating the unreacted fructose from the reaction mixture solution after the reaction.

Comparative Example 4: HMF Preparation from Fructose Using Isopropyl Alcohol Isopropyl Fructose (15 g) was mixed with isopropanol (IPA; 100 g) and Amberlyst-15 resin (1 g), and reacted by heating at 100° C. for 5 hours to prepare HMF. Upon reaction, the resulting solution was cooled to room temperature and then filtered to separate Amberlyst-15 resin from the reaction mixture solution. The separated reaction mixture solution was analyzed via liquid chromatography and the resulting yield of the synthesized HMF was 42%.

Conclusively, the HMF yield was much lower when using IPA as a solvent compared to when using 1-butanol as a solvent, although the same solid acid catalyst was used. Additionally, since fructose is dissolved in IPA, there was a difficulty in separating the unreacted fructose from the reaction mixture solution after the reaction. Furthermore, since IPA has a boiling point of 82.6° C., it is difficult to use IPA as a solvent in order to maintain the reaction temperature at 100° C. or higher under ambient pressure, and may subsequently cause the loss of the solvent due to its volatility, thus exhibiting a limitation to be used in the process of HMF preparation.

Comparative Example 5: HMF Preparation from Fructose Using Gamma-Valerolactone Solvent Fructose (15 g) was mixed with gamma-valerolactone (GVL; 100 g) and Amberlyst-15 resin (1 g), and reacted by heating at 100° C. for 5 hours to prepare HMF. Upon reaction, the resulting solution was cooled to room temperature and then filtered to separate Amberlyst-15 resin from the reaction mixture solution. The separated reaction mixture solution was analyzed via liquid chromatography and the resulting yield of the synthesized HMF was 55%.

Conclusively, the HMF yield was much lower when using GVL as a solvent compared to when using 1-butanol as a solvent, although the same solid acid catalyst was used. Additionally, since fructose is dissolved in GVL, there was a difficulty in separating the unreacted fructose from the reaction mixture solution after the reaction.

Comparative Example 6: HMF Preparation from Glucose Using a Water Solvent

Glucose (15 g) was mixed with water (100 g), Sn-beta zeolite (1 g) and Amberlyst-15 resin (1 g), and reacted by heating at 130° C. for 5 hours to prepare HMF. Upon reaction, the resulting solution was cooled to room temperature and then filtered to separate Sn-beta zeolite and Amberlyst-15 resin from the reaction mixture solution. The separated reaction mixture solution was analyzed via liquid chromatography and the resulting yield of the synthesized HMF was 20%.

Conclusively, the HMF yield was much lower when using glucose instead of fructose, and accordingly, subsequently further using Sn-beta zeolite isomerization catalyst while using water as a solvent, compared to when using 1-butanol as a solvent, although the same solid acid catalyst was used, as is the cases with the results obtained in the preparation methods using fructose as a reactant.

The invention claimed is:

1. A method for preparing a furan derivative from biomass, comprising:
    step (1) of preparing 5-hydroxymethylfurfural by reacting biomass and a solid acid catalyst in butanol; and
    step (2) of preparing a furan derivative by reacting the butanol solution of 5-hydroxymethylfurfural, obtained in step (1), with a hydrogenation catalyst,
    wherein the furan derivative is dimethylfuran or dihydroxymethylfuran,
    wherein the method further comprises step (1-1), which is to remove the solid acid catalyst and unreacted biomass from the reaction mixture of step (1), before step (2), or
    wherein the method further comprises step (2-1), which is to separate the furan derivative from the butanol, after step (2).

2. The method of claim 1, wherein the biomass is fructose, glucose, or both fructose and glucose.

3. The method of claim 1, wherein the solid acid catalyst is bronsted acid, Lewis acid, or a mixture thereof.

4. The method of claim 1, wherein the solid acid catalyst is an ion exchange resin type.

5. The method of claim 1, wherein the biomass and the butanol are used at a weight ratio of from 1:1 to 1:100.

6. The method of claim 1, wherein the butanol is 1-butanol or isobutanol.

7. The method of claim 1, wherein step (1) is performed at a temperature from 50° C. to 100° C. at ambient pressure.

8. The method of claim 1, wherein step (1-1) is performed by filtration at a temperature from 10° C. to 50° C.

9. The method of claim 1, wherein step (2-1) is performed by fractional distillation and crystallization.

10. A method for preparing 5-hydroxymethylfurfural comprising reacting biomass and a solid acid catalyst in butanol and removing the solid acid catalyst and unreacted biomass from a reaction mixture.

11. A method for preparing a furan derivative comprising reacting 5-hydroxymethylfurfural dissolved in butanol with a hydrogenation catalyst,
    wherein the furan derivative is dimethylfuran or dihydroxymethylfuran, or
    wherein the hydrogenation catalyst is a heterogeneous catalyst comprising one or more metal component(s) selected from the group consisting of Ru, Pt, Au, Pd, Cu, and Ni.

* * * * *